United States Patent [19]

Schroëder et al.

[11] Patent Number: 5,110,975

[45] Date of Patent: May 5, 1992

[54] ISOCYANATOALKYL SULPHONATES AND A PROCESS FOR THEIR PREPARATION

[75] Inventors: Georg Schroëder, Burscheid-Hilgen; Dieter Arlt, Cologne; Manfred Jautelat, Burscheid, all of Fed. Rep. of Germany

[73] Assignee: Bayer Aktiengesellschaft, Leverkusen, Fed. Rep. of Germany

[21] Appl. No.: 626,493

[22] Filed: Dec. 12, 1990

[30] Foreign Application Priority Data

Dec. 22, 1989 [DE] Fed. Rep. of Germany ... 39-42465

[51] Int. Cl.$^5$ ............... C07C 303/00; C07C 307/00; C07C 309/00; C07C 311/00
[52] U.S. Cl. ........................... 558/44; 558/49; 558/50; 558/51; 558/52; 558/57; 558/58
[58] Field of Search ............ 558/44, 49, 50, 51, 558/52, 57, 58

[56] References Cited

U.S. PATENT DOCUMENTS 4,424,167  1/1984  Oecki ..................... 558/303

OTHER PUBLICATIONS

Rompps Chemi-Lexikon, Dr. Otto-Albrecht Neumuller, Acht, Nuebearbeitete und erweiterte Auflage, Franchk'sche Verlagshandlung, Stuttgart 1987 pp. 4183 and 4188.

Primary Examiner—Mary C. Lee
Assistant Examiner—Robert C. Whittenbaugh
Attorney, Agent, or Firm—Sprung Horn Kramer & Woods

[57] ABSTRACT

Isocyanatoalkyl sulphonates of the general formula $$OCN-X-(CH_2)_n-O-\overset{\overset{\displaystyle O}{\|}}{\underset{\underset{\displaystyle O}{\|}}{S}}-A \qquad I$$

wherein the substituent meanings are as given in the description are obtained by reacting the corresponding isocyanatoalkyl halides with sulphonic acid esters of the formula $$A-\overset{\overset{\displaystyle O}{\|}}{\underset{\underset{\displaystyle O}{\|}}{S}}-O-R^3$$

wherein $R^3$ has the meanings given in the description. They are used as cross-linking agents in polyamines.

2 Claims, No Drawings

ISOCYANATOALKYL SULPHONATES AND A PROCESS FOR THEIR PREPARATION

It is known that sulfonic acid esters are accessible from the corresponding alcohols by esterification with sulfonic acid chlorides[R.K. Crossland, K. L.Servis, J. Org. Chem., 35, 3195 (1970)] or sulfonic acid anhydrides [R. C. Paul, S. K. Sharma, R. D. Sharma, K. C. Malhotra, Chem. Ind., 1971, 702]. It would be expected that the isocyanatoalkyl sulfonates which are to date still unknown can be prepared only with difficulty by this route, since the hydroxyalkyl isocyanates required as educts for their preparation are as a rule very labile [U.S. Pat. Specification No. 4,250,105; F. W. Hoover, H. B. Stevenson, H. S. Rothrock, J. Org. Chem., 28, 1825 (1963)] and the formation of chloroalkylcarbamoyl chlorides is to be expected during the preparation. A proportion of oligomeric material must moreover be expected during the preparation [U.S. Pat. Specification No.

Alternative processes for the preparation of sulfonates are generally known, thus, for example, by reaction of halides with silver sulfonates or copper(I) sulfonates [P. W. Feit, O. T. Nelson, J. Med. Chem., 9, 416 (1966); Japanese Patent Specification 59/73,587; and CA 101, 130519]. Catalysed nucleophilic exchange of halides for sulfonates in isocyanatoalkyl halides has been found as a possible means of access to the isocyanatoalkyl sulfonates which are to date still unknown. The exchange reaction has todate been employed merely for simple alkyl halides [R. C. Hahn, J. Org. Chem., 53, 5783 (1988)]. Because of the high reactivity of the isocyanate group, it had to be feared that the isocyanates would trimerize under the influence of the catalysts used W. Broda, E. V. Dehmlow, H. J. Schulz, Isr. J. Chem., 26, 222 (1985)]. Surprisingly, it has been found that the trimerization of the isocyanate groups can be suppressed under the conditions described below, in spite of the influence of the catalysts, and the isocyanatoalkyl sulfonates can thus be prepared.

The present invention relates to new isocyanatoalkyl sulfonates of the general formula

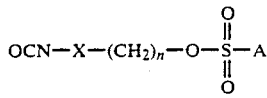

wherein
X represents a branched or unbranched alkylene group having 1–18 C atoms, a cycloalkylene group having 5–14 C atoms or an arylene radical having 6–20 C atoms, each of which can optionally be substituted by $C_1$–$C_4$-alkyl, $COOR^1$ or $OR^2$, wherein $R^1$ and $R^2$ independently of one another represent a $C_1$–$C_4$-alkyl radical,
n represents an integer from 1 to 3 and
A represents an alkyl group having 1–18 C atoms, a cycloalkyl group having 5–14 C atoms, an aryl radical having 6–20 C atoms or an aralkyl group having 7–16 C atoms, each of which can optionally be substituted by a carboxamido, alkoxy, cyano or carboxylic acid ester group,
and to a process for the preparation of isocyanatoalkyl sulfonates of the general formula I, which is characterized in that an isocyanatoalkyl halide of the general formula $$OCN-X-(CH_2)_n-Y \qquad (II)$$

wherein X has the meaning given in formula I and
Y represents chlorine, bromine or iodine,
is reacted with a sulfonic acid ester of the general formula

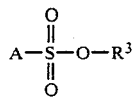

wherein
A has the meaning given in formula I and
$R^3$ represents an alkyl group having 1–18 C atoms, a cycloalkyl group having 5–14 C atoms, an aryl radical having 6–20 C atoms or an aralkyl group
preferably in the presence of a catalyst of the general formula

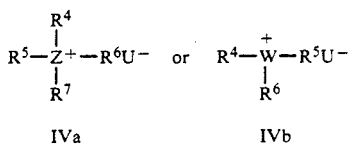

wherein
$R^4$ to $R^7$ independently of one another for an alkyl group having 1–18 C atoms, a cycloalkyl group having 5–14 C atoms, an aryl radical having 6–20 C atoms or an aralkyl group having 7–16 C atoms, or
$R^4$ represents the radical of a polymer which contains at least one group

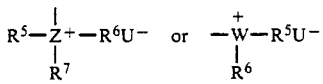

bonded to a C atom of the polymer chain,
Z represents nitrogen, phosphorus or arsenic,
W represent S or S=0
U represents Cl, Br, I or B, wherein
B represents the formula $R^8-SO_3^{\ominus}-$ and $R^8$ represents an alkyl group having 1–18 C atoms, a cycloalkyl group having 5–14 C atoms, an aryl radical having 6–20 C atoms or an aralkyl group having 7–16 C atoms.

Preferably, 1 mol of II is reacted with 0.1 to 10 mol of III in the presence of 0.001 to 0.5 mol of IV at about 50 to 200° C.

If appropriate, the reaction is carried out in the presence of an inert diluent, for example N,N- o dimethylformamide, N,N-dimethylacetamide, dimethyl sulfoxide, N-methylpyrrolidone, dimethoxyethane, diethylene glycol dimethyl ether and the like. The reaction times are in general several hours, depending on the temperature and catalyst concentration. I is preferably separated off by distillation, but can also be separated off by chromatography or by crystallization. It may also be advantageous subsequently to increase the amount of catalyst of the general formula IV stepwise in the course of the reaction.

Preferred compounds are those in which

X represents an alkylene group having 1-7 C atoms, a cycloalkylene group having 5-6 C atoms, or an arylene radical having 6-10 C atoms which can optionally be substituted by a $C_1$-$C_2$-alkyl radical, $COOR^1$ or $OR^2$, wherein
$R^1$ and $R^2$ independently of one another represent a $C_1$-$C_4$-alkyl radical,
n represents the number 1 or 2 and
Y represents chlorine or bromine.

Starting compounds which may be mentioned specifically are: 4-chloro-isocyanatobutane, 5-chloro-isocyanatopentane, 1-chloro-2-isocyanatopropane, 2-chloroisocyanatopropane, 1-chloro-2-isocyanatobutane, 3-chloro2,2-dimethylisocyanatopropane, 3-chloro-2-isocyanatoLe propane, 3-isocyanatoiodopropane, 2-bromo-isocyanatoethane, 3-bromo-isocyanatopropane, 4-bromo-isocyanatobutane,5-bromo-isocyanatopentane,4-chloro-methyl-phenyl isocyanate and 3-chloro-methyl-phenyl isocyanate. 2-Chloro-isocyanatoethane, 3-chloro-isocyanatopropane and 6-chloro-isocyanatohexane may be mentioned as particularly preferred.

Compounds of the formula III which are preferably employed are those wherein
A and $R^3$ independently of one another represent an alkyl group having 1-6 C atoms, a cycloalkyl group having 5-6 C atoms, an aryl radical having 6-10 C atoms or an aralkyl group having 7-10 C atoms.

Compounds which may be mentioned specifically are: propyl methanesulfonate, methyl ethanesulfonate, ethyl ethanesulfonate, propyl ethanesulfonate, methyl propanesulfonate, ethyl propanesulfonate, propyl propanesulfonate, methyl 4-toluenesulfonate, ethyl 4-toluenesulfonate, propyl 4-toluenesulfonate, methyl benzenesulfonate, ethyl benzenesulfonate and propyl benzenesulfonate. Methyl methanesulfonate and ethyl methanesulfonate may be mentioned as particularly preferred here.

Compounds of the formula IV which are preferably employed are those wherein
$R^4$ and $R^7$ independently of one another represent an alkyl group having 1-12 C atoms, a cycloalkyl group having 5-10 C atoms, an aryl radical having 6-10 C atoms or an aralkyl group having 7-10 C atoms,
or
$R^4$ represents a polymeric structure,
Z represents nitrogen, phosphorus or arsenic and
U represents chlorine, bromine, iodine or B, wherein
B represents the formula $R^8$—$SO_3^\ominus$— and $R^8$ represents an alkyl group having 1-12 C atoms, a cyclo-alkyl group having 5-10 C atoms, an aryl radical having 6-10 C atoms or an aralkyl group Starting compounds which may be mentioned specifically are: tetramethylammonium chloride, tetramethylammonium bromide, tetramethylammonium iodide, tetramethylammonium methanesulfonate, tetraethylammonium chloride, tetraethylammonium bromide, tetraethylammonium iodide, tetraethylammonium methanesulfonate, tetrapropylammonium chloride, tetrapropylammonium bromide, tetrapropylammonium iodide, tetrapropylammonium ethanesulfonate, tetrabutylammonium chloride, tetrahexylammonium chloride, tetrahexylammonium bromide, tetrahexylammonium methanesulfonate, tetrabutylphosphonium chloride, tetrabutylphosphonium iodide and tetrabutylphosphonium methanesulfonate. Tetrabutylammonium bromide, tetrabutylammonium iodide, tetrabutylammonium methanesulfonate, tetrahexylammonium iodide and tetrabutylphosphonium bromide may be mentioned as being particularly preferred here.

Examples of suitable high molecular weight compounds IV are the products which are obtainable by reaction of optionally crosslinked (for example with divinylbenzene) chloromethylated styrene homopolymers or styrene copolymers with compounds of the formula

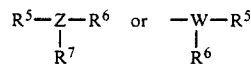

The isocyanatoalkyl halides are known or can be prepared by known processes compare, for example, Houben-Weyl, vol. E4, page 738 et seq.; W. Siefken, Liebigs Ann. Chem., 562, 72 (1949); H. Wenker, J. Am. Chem. Soc., 58, 2608 (1936); O. Bayer, Angew. Chem., 59, 257 (1947); H. Najer, P. Chabrier, R. Guidicelli, Bull. Soc. Chim. Fr., 1959, 1611; German Patent 947,470; German Specification 3,326,874; K. D. Kampe, Liebigs Ann. Chem., 752, 142 (1971); A. Krantz, B. Hoppe, Tetrahedron Lett., 1975, 695; C. K. Johnson, J. Org. Chem., 32 (5), 1508, (1967); and H. R. Kricheldorf, Angew. Chem., 91, 749 (1979).

The new compounds of the general formula I are used, for example, as crosslinking agents in the preparation of polymers. Agents for finishing paper, for example, can thus be obtained by reaction of polyamidoamines or polyamines analogously to the reaction with other bifunctional crosslinking agents, for example epichlorohydrin.

Suitable starting components and process conditions are described, for example, in the following literature references: DE-A 2,229,219, 1,771,043, 2,257,271, 2,938,588, 2,949,870, 1,720,905 and 1,906,450, 0,131,200 and 0,126,176 and U.S. Pat. Specifications No. 2,926,154 and 3,332,901.

EXAMPLE 1

Preparation of 2-isocyanato-methanesulfonyloxyethane 20.0 g (0.06 mol) of tetrabutylammonium methanesulfonate are added to a solution of 36.0 g (0.34 mol) of 2-chloroisocyanatoethane and 93.3 g (0.85 mol) of methyl methanesulfonate and the mixture is heated at 120° C for 6 hours. It is distilled in a thin layer evaporator at 180° C. under a pressure of 0.04 mbar and the crude product is purified by distillation. 18.0 g (0.17 mol) of 2chloroisocyanatoethane and 71.0 g (0.65 mol) of methyl methanesulfonate are recovered in this way.

Yield: 10.50 g (0.06 mol, 35% of theory)
Boiling point: 97° C. (0.05 bar)
$^1$H-NMR: ($CDCl_3$, 200 MHz) $\delta = 3.10$ (s; 3H), 2.66 (t, J=5 Hz; 2H) 4.32 (t, J=5 Hz; 2H)
$^{13}$C-NMR ($CDCl_3$, 50 HHz) $\delta = 37.65$, 42.36, 68.18, 121.0
IR: 2260 (s), 1340 (s), 1165 (s), 1015 (s), 960 (s), 900 (s), 790 (s)

EXAMPLE 2

Preparation of 3-isocyanato-methanesulfonyloxyprooane 28.4 g (0.084 mol) of tetrabutylammonium methanesulfonate are added to a solution of 100.0 g (0.84 mol) of 3-chloroisocyanatopropane and 92.4 g (0.84 mol) of methyl methanesulfonate and the mixture is heated at 120° C. for 14 hours.

The mixture is distilled on a thin film evaporator at 180° C. under a pressure of 0.04 mbar and the crude product is purified by distillation. 22.85 g (0.21 mol) of methyl methanesulfonate and 5.3 g (0.04 mol) of 3-chloroisocyanatopropane are recovered in this way.

Yield: 48.00 g (0.27 mol, 33% of theory)
Boiling point: 102°-104° C. (0.04 mbar)
$^1$H-NMR: (CDCl$_3$, 200 MHz) $\delta = 2.02$ (q, J=5 Hz; 2H), 3.10 (s; 3H); 3.55 (t, J=5 Hz; 2H); 4.35 (t; J=5 Hz; 2H)
$^{13}$C-NMR (CDCl$_3$, 50 MHz) $\delta = 30.38, 37.22, 39.23, 66.69, 121.0$
IR: 2260 (s), 1340 (s), 1165 (s), 101 (s), 970 (s), 940 (s)

EXAMPLE 3

Preparation of 6-isocyanatomethanesulfonyloxyhexane 50.0 g (0.15 mol) of tetrabutylammonium methanesulfonate are added to a solution of 242.25 g (1.50 mol) of 6-chloroisocyanatohexane and 165.00 g (1.50 mol) of methyl methanesulfonate and the mixture is heated at 140° C. for 16 hours.

The mixture is filtered over silica gel, the column is eluted with ethyl acetate/cyclohexane (1:3; volume:volume) and the crude product is purified by distillation. 99.3 g (0.61 mol) of 6-chloroisocyanatohexane are recovered in this way.

Yield: 74.80 g (0.34 mol, 38% of theory)
Boiling point: 123-137° C.(0.1 mbar)
$^1$H-NMR: (CDCl$_3$, 200 MHz) $\delta = 1.45$ (mc; 4H), 163 (mc; 2H), 1.77 (mc; 2H), 3.01 (s; 3H), 3.33 (t, J=5.5 Hz; 2H) 4.24 (t, J=5.5 Hz; 2H)
$^{13}$C-NMR (CDCl$_{13}$, 50 MHz) $\delta = 24.85, 25.98, 28.97, 30.99, 7.07, 42.84, 70.30, 121.96,$
IR: 2940 (s), 2290 (s), 1360 (s), 1185 (s), 990 (s), 4965 (s), 930 (s).

We claim:
1. 1. Sulfonate isocyanates of the formula

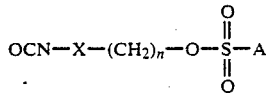

wherein
X represents a branched or unbranched alkylene group having 1-18 C atoms, a cycloalkylene group having 5-14 C atoms or an arylene radical having 6-20 C atoms, each of which can optionally be substituted by C$_1$-C$_4$-alkyl, COOR$^1$ or OR$^2$, wherein R$^1$ and R$^2$ independently of one another represent a C$_1$-C$_4$-alkyl radical,
n represents an integer from 1 to 3 and
A represents an alkyl group having 1-18 C atoms, a cycloalkyl group having 5-14 C atoms, an aryl radical having 6-20 C atoms or an aralkyl group having 7-16 C atoms, each of which can optionally be substituted by a carboxamido, alkoxy, cyano or carboxylic acid ester group.

2. Process for the preparation of the isocyanates of claim 1, characterized in that an isocyanate-halide of the formula

wherein X has the meaning given in claim 1 and
Y represents chlorine, bromine or iodine,
is reacted with a sulfonic acid ester of the general formula

wherein
A has the meaning given in claim 1 and
R$^3$ represents an alkyl group having 1-18 C atoms, a cycloalkyl group having 5-14 C atoms, an aryl radical having 6-20 C atoms or an aralkyl group having 7-16 C atoms,
preferably in the presence of a catalyst of the general formula

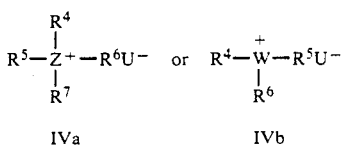

wherein
R$^4$ to R$^7$ independently of one another for an alkyl group having 1-18 C atoms, a cycloalkyl group having 5-14 C atoms, an aryl radical having 6-20 C atoms or an aralkyl group having 7-16 C atoms, or
R$^4$ represents the radical of a polymer which contains at least one group

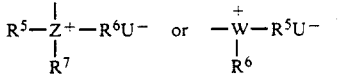

bonded to a C atom of the polymer chain,
Z represents nitrogen, phosphorus or arsenic,
W represents S or S=O,
U represents Cl, Br, I or B,
wherein
B represents the formula R$^8$—SO$_3^\ominus$— and R$^8$ represents an alkyl group having 1-18 C atoms, a cycloalkyl group having 5-14 C atoms, an aryl radical having 6-20 C atoms or an aralkyl group having 7-16 C atoms.

* * * * *

UNITED STATES PATENT AND TRADEMARK OFFICE
CERTIFICATE OF CORRECTION

PATENT NO. : 5,110,975
DATED : May 5, 1992
INVENTOR(S) : Schroder, et al.

It is certified that error appears in the above-identified patent and that said Letters Patent is hereby corrected as shown below:

Title Page    Applicant: Delete " Schroeder et al. " and sub-
              situte -- Schroder et al. --

Item          [75] Inventors: 1st Inventor delete " Schroeder "
              and substitute -- Schroder --

Signed and Sealed this

Sixteenth Day of August, 1994

Attest:

BRUCE LEHMAN

Attesting Officer    Commissioner of Patents and Trademarks